United States Patent [19]

Mühlbauer

[11] Patent Number: 5,591,027
[45] Date of Patent: Jan. 7, 1997

[54] DELIVERY SYRINGE FOR DENTAL COMPOUND

[76] Inventor: Ernst Mühlbauer, Elbgaustrasse 248, 22547 Hamburg, Germany

[21] Appl. No.: 420,354

[22] Filed: Apr. 11, 1995

[30] Foreign Application Priority Data

Apr. 15, 1994 [DE] Germany ............................ 9406342 U

[51] Int. Cl.⁶ ............................................. A61C 5/04
[52] U.S. Cl. ............................................. 433/90
[58] Field of Search ..................... 433/26, 89, 90; 206/571, 63.5, 364, 368, 369

[56] References Cited

U.S. PATENT DOCUMENTS

| | | | |
|---|---|---|---|
| 4,391,590 | 7/1983 | Dougherty | 433/90 |
| 4,472,141 | 9/1984 | Dragan | 433/90 |
| 4,492,576 | 1/1985 | Dragan | 433/90 |
| 4,801,263 | 1/1989 | Clark | 433/90 |
| 4,863,072 | 9/1989 | Perler | 433/90 X |
| 5,083,921 | 1/1992 | Dragan | 433/90 |
| 5,199,567 | 4/1993 | Discko, Jr. | 206/369 |
| 5,267,859 | 12/1993 | Discko, Jr. | 433/89 |
| 5,364,267 | 11/1994 | Fischer | 433/26 |
| 5,464,348 | 11/1995 | Fischer et al. | 433/26 |

FOREIGN PATENT DOCUMENTS 2741185  2/1979  Germany ..................... A61C 5/04

Primary Examiner—Nicholas D. Lucchesi
Attorney, Agent, or Firm—Chilton, Alix & Van Kirk

[57] ABSTRACT

Delivery syringe for dental compound, especially for fillings and veneers, the plunger of which is displaceable by a screw spindle exhibiting a handle. The handle is configured, according to the invention, as a color sample for the dental compound contained in the delivery syringe. To enable a sufficient turning force to be applied to the spindle even by means of a narrow color sample, the syringe body, in order to reduce the necessary turning force, is expediently configured such that it is free from any constriction.

2 Claims, 1 Drawing Sheet

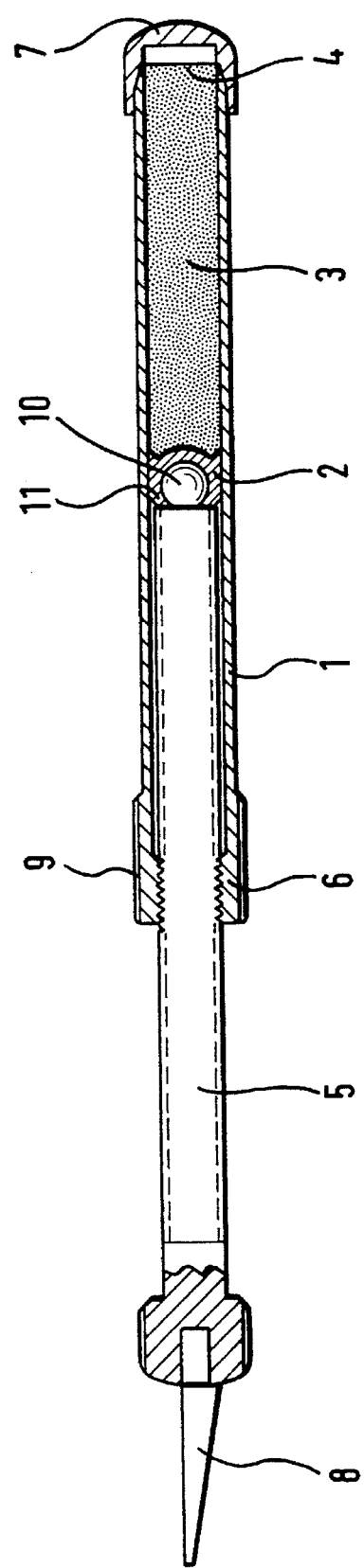

1

DELIVERY SYRINGE FOR DENTAL COMPOUND

The invention relates to a delivery syringe for dental compound, the plunger of which is displaceable by a screw spindle which can be twisted by means of a handle.

In order to be able to match the colour of filling compound or veneering material as accurately as possible to the colour of the teeth of the patient, the dentist has at his disposal a host of correspondingly colour-matched dental compounds and associated colour samples, which are combined, for example, in the style of a fan, in a so-called "tooth-colour ring". The individual samples are narrow platelets which are tapered into a flat wedge shape and the shape of which is not dissimilar to an incisor. They can thus be isolated on the tooth-colour ring in such a way that they can be kept separate from the other samples for comparison against the teeth. They carry alphanumerical notations which make it possible to assign to them that delivery syringe containing the correspondingly colour-matched dental compound. In the execution of this assignment, errors can be made. The invention seeks therefore a facility for making it easier to assign the sample and the delivery syringe.

The solution according to the invention consists in the handle of the screw spindle including a colour sample for the dental compound contained in the delivery syringe. The dentist uses the handle, i.e. the rear end of the delivery syringe, as a colour sample. As soon as he has found the right sample, he is also already holding the right delivery syringe. He is spared from making an assignment on the basis of colour codes; assignment errors are precluded. If he or his assistant has made a selection, this can be verified again directly when he has the delivery syringe in his hand.

Although it is possible to configure the sample in the form of known handles for turning the spindle, which handles are configured for example as a pair of wings, it is more convenient for comparison with the tooth colour if the sample adjoins the spindle in the rearward direction, roughly in the longitudinal direction of the said spindle.

To ensure that, despite the narrowness of the sample, the spindle is able to be easily turned even where a considerable torque is necessary for this, additional manipulation parts can be provided. It is more expedient however if no further parts, or only small ones, of a handle need to be provided, and the spindle is able to be turned purely by means of the colour sample. This is only however possible where the turning force required by the spindle is small. This is achieved according to the invention by the fact that the syringe body opens out into the discharge opening free from any constriction. This allows the spindle even to be twisted with one hand, despite the narrowness of the colour sample. A constriction-free discharge opening has hitherto been known only in respect of granular substances such as amalgam or bone chips U.S. Pat. No. 4,801,263, DE-B 27 41 185)

BRIEF DESCRIPTION OF THE DRAWING

The invention is explained in greater detail below with reference to the drawing, the figure of which illustrates the delivery syringe of the present invention, partially broken away and partially in section.

The syringe body 1 contains a plunger 2, which, in order to discharge the viscous dental compound 3 out of the discharge opening 4 of the syringe body 1, is displaceable by means of a threaded spindle 5, which can be screwed in the nut part 6 of the syringe body 1. The discharge opening 4 of the syringe body 1 can be closed off by means of a cap 7.

At the rear end, the spindle 5 is connected in a rotationally secure manner to a colour sample 8, which has the incisor-like shape which is known for such colour samples; i.e. possesses a width of 7 mm, for example, and a length of 10 mm, for example, the said colour sample tapering towards its end into a flat wedge shape, i.e. having a thickness between about 3 mm at its front end and about 0.5 mm at its free end. These measurements could also of course be chosen differently, where this would appear advantageous for sampling or manipulation purposes. It has been shown, however, that even when configured in this traditional form, the sample body, as a handle for twisting the spindle 5, is in any event adequate where the syringe body 1 is configured such that it is free from constriction up to its discharge opening 4. In this case, indeed, only a small torque upon the spindle 5 is necessary for the viscous dental compound to be discharged.

Manipulation wings on the spindle are in this case dispensable, nor do they need to be provided on the syringe body. A longitudinal fluting 9 on the syringe body is all that is needed. Additionally, if appropriate, a rotary knob arranged between the spindle 5 and the sample 8 can be provided with a longitudinal fluting. Since the syringe, owing to the absence of the projecting manipulation wings, has a smaller lateral spatial requirement, it is able to be packed in a more space-saving manner than conventional types. This advantage is irrespective of the design of the spindle handle as a colour sample. The combination of the constriction-free design of the syringe body and the absence of laterally projecting handles on the syringe body and spindle is therefore, where appropriate, deserving of protection, irrespective of the design of the spindle handle as a colour sample.

At the front end of the spindle 5, this is fixedly provided with a spherically configured coupling part 10, which can be snap-locked into a corresponding coupling cavity on the plunger 2 whenever the plunger is outside the syringe body. With a constricted cross-sectional part 11, the plunger reaches behind the spherical coupling part 10. When the plunger is within the syringe body 1, the constricted, rear part of the plunger is prevented from elastically expanding. Spindle 5 and plunger 2 are thereby joined together in a traction-resistant arrangement. This design has the advantage that the plunger can not only be advanced to eject the compound from the syringe body, but can also be retracted. This is of importance, for example, where the user discovers that he has forced out of the syringe body more of the expensive compound than is necessary for the particular application. By retraction of the plunger, the excess is able to be sucked back into the syringe body in order to be preserved for the following application.

The colour sample can be glued or bonded to the spindle. Additionally or instead, a positive-locking connection can also be provided, into which the colour sample is snap-locked, clamped or latched (preferably non-detachably).

I claim:

1. A delivery syringe for a dental compound, especially for fillings and veneers, comprising a syringe body (1) having an elongated cavity for holding the dental compound, said cavity having an internally threaded proximal end and a non-constricted distal delivery end contiguous with the elongated cavity, a removable end cap for closing said delivery end, a screw spindle (5) mounted on the body and having an external drive thread operatively associated with said internally threaded cavity for driving movement of the spindle relative to said body, and a plunger (2) mounted in the syringe body for displacement by the screw spindle (5), said spindle having a free end for rotatably driving the spindle relative to the body, said free end having thereon a color sample (8) for the dental compound (3) contained in the delivery syringe, said syringe body and said spindle being free of any lateral projection extending beyond the perimeter of said end cap.

2. Delivery syringe according to claim 1, characterized in that the spindle is an elongated member and the color sample (8) adjoins the free end of the spindle (5) substantially in the longitudinal direction of the said spindle, said color sample being a flatly configured, narrow member facilitating rotational movement of said spindle.

* * * * *